United States Patent
Ryu et al.

(10) Patent No.: US 9,925,368 B2
(45) Date of Patent: Mar. 27, 2018

(54) BIO-IMPLANTABLE ELECTRODE ASSEMBLY

(71) Applicant: INNOTHERAPY INC., Seoul (KR)

(72) Inventors: Seong Woo Ryu, Seoul (KR); Hae Shin Lee, Daejeon (KR); Moon Sue Lee, Seoul (KR); Sun Ha Paek, Seoul (KR); Mi Young Koh, Incheon (KR)

(73) Assignee: INNOTHERAPY INC., Seoul (KR)

( * ) Notice: Subject to any disclaimer, the term of this patent is extended or adjusted under 35 U.S.C. 154(b) by 0 days.

(21) Appl. No.: 14/895,591

(22) PCT Filed: Jun. 3, 2014

(86) PCT No.: PCT/KR2014/004972
§ 371 (c)(1),
(2) Date: Dec. 3, 2015

(87) PCT Pub. No.: WO2014/196812
PCT Pub. Date: Dec. 11, 2014

(65) Prior Publication Data
US 2016/0129241 A1     May 12, 2016

(30) Foreign Application Priority Data
Jun. 4, 2013    (KR) .................. 10-2013-0064275

(51) Int. Cl.
*A61N 1/05*  (2006.01)
*A61N 1/36*  (2006.01)
(Continued)

(52) U.S. Cl.
CPC ......... *A61N 1/0551* (2013.01); *A61N 1/0534* (2013.01); *A61N 1/3605* (2013.01);
(Continued)

(58) Field of Classification Search
CPC ............... A61N 1/3605; A61N 1/0551; A61N 2007/0021
See application file for complete search history.

(56) References Cited

U.S. PATENT DOCUMENTS 6,361,861 B2    3/2002  Gao et al.
7,787,959 B1 *  8/2010  Morgan ............... A61N 1/0556
                                                      607/116
(Continued)

FOREIGN PATENT DOCUMENTS

CN    101927057 A    12/2010
CN    103079462 A    5/2013
(Continued)

OTHER PUBLICATIONS

Liu et al., "Carbon nanotube yarns with high tensile strength made by a twisting and shrinking method" IOP Publishing, Nanotechnology 21 (2010) 045708 pp. 1-7.
(Continued)

*Primary Examiner* — Michael Carey
*Assistant Examiner* — Natasha Patel
(74) *Attorney, Agent, or Firm* — STIP Law Group, LLC

(57) ABSTRACT

Disclosed is a carbon material for a neurostimulation electrode. The carbon material is composed of a carbon fiber. The carbon fiber has a thickness of 1 to 1000 μm, a linear density of 0.01 to 5.00 g/cm, and an aspect ratio of 100 to 1,000,000. Particularly, the carbon fiber material can be obtained by dry spinning carbon nanotubes, followed by liquid-based densification. The carbon material can be used in the fields of deep brain stimulation, spinal cord stimulation, etc. Also disclosed are an electrode assembly and a neurostimulation device, each including the carbon material.

13 Claims, 4 Drawing Sheets

(51) Int. Cl.
*B82Y 15/00* (2011.01)
*A61N 1/08* (2006.01)

(52) U.S. Cl.
CPC .......... *A61N 1/086* (2017.08); *A61N 1/36171* (2013.01); *B82Y 15/00* (2013.01)

(56) References Cited

U.S. PATENT DOCUMENTS

| | | | |
|---|---|---|---|
| 2003/0055457 A1* | 3/2003 | MacDonald | A61N 1/368 607/2 |
| 2007/0166223 A1 | 7/2007 | Jiang et al. | |
| 2008/0170982 A1* | 7/2008 | Zhang | B82Y 10/00 423/447.3 |
| 2008/0183258 A1* | 7/2008 | Inman | A61N 1/0558 607/118 |
| 2008/0288067 A1 | 11/2008 | Flood | |
| 2010/0276633 A1 | 11/2010 | Pick | |
| 2011/0034969 A1 | 2/2011 | Capcelea et al. | |
| 2011/0186775 A1 | 8/2011 | Shah et al. | |
| 2012/0035726 A1* | 2/2012 | Gross | A61F 2/1624 623/6.63 |
| 2012/0053649 A1 | 3/2012 | Liu et al. | |
| 2013/0090542 A1 | 4/2013 | Kipke et al. | |
| 2013/0110215 A1 | 5/2013 | Fan et al. | |
| 2014/0303470 A1* | 10/2014 | Tsukada | A61B 5/0408 600/377 |

FOREIGN PATENT DOCUMENTS

| | | |
|---|---|---|
| CN | 103093865 A | 5/2013 |
| JP | 2009529352 A | 8/2009 |
| KR | 10-2010-0065678 A | 6/2010 |
| KR | 1020080124133 A | 6/2010 |
| WO | WO2007111107 A1 | 10/2007 |
| WO | WO2009107846 A1 | 9/2009 |

OTHER PUBLICATIONS

Rezai et al. "Neurostimulation Systems for Deep Brain Stimulation: In Vitro Evaluation of Magnetic Resonance Imaging-Related Heating at 1.5 Tesla", Journal of Magnetic Resonance Imaging 15:241-250 (2002) pp. 241-250.

Zhang et al; Multifunctional Carbon Nanotube Yarns by Downsizing an Ancient Technology; Science; Nov. 19, 2004; vol. 306, Issue 5700, pp. 1358-1361; AAAS, USA.

* cited by examiner

[Fig. 1]
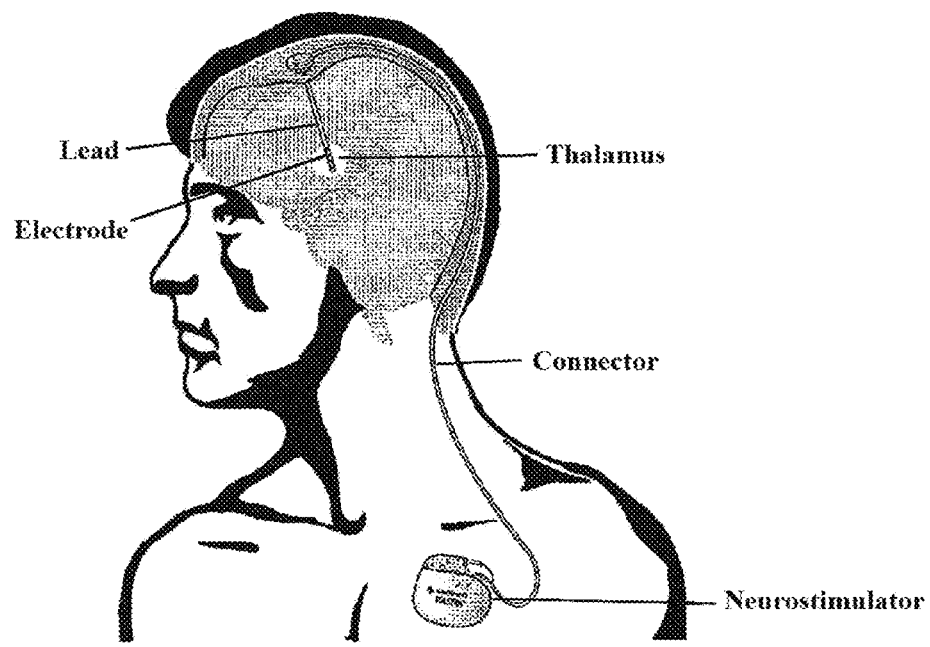
[Fig. 2]
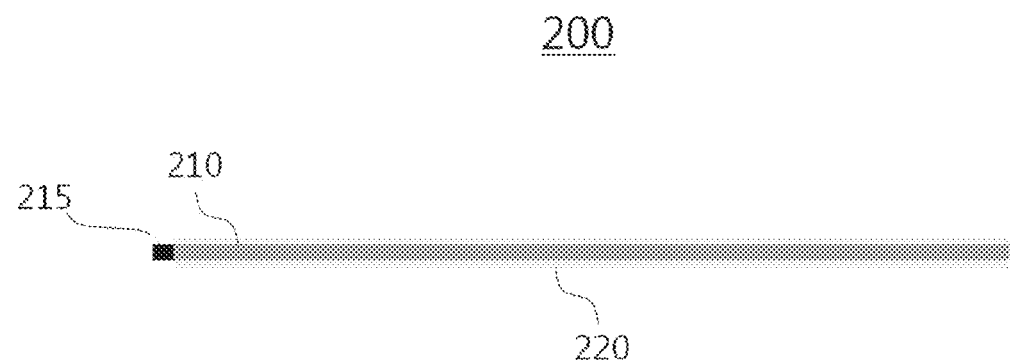

[Fig. 3]
[Fig. 4]
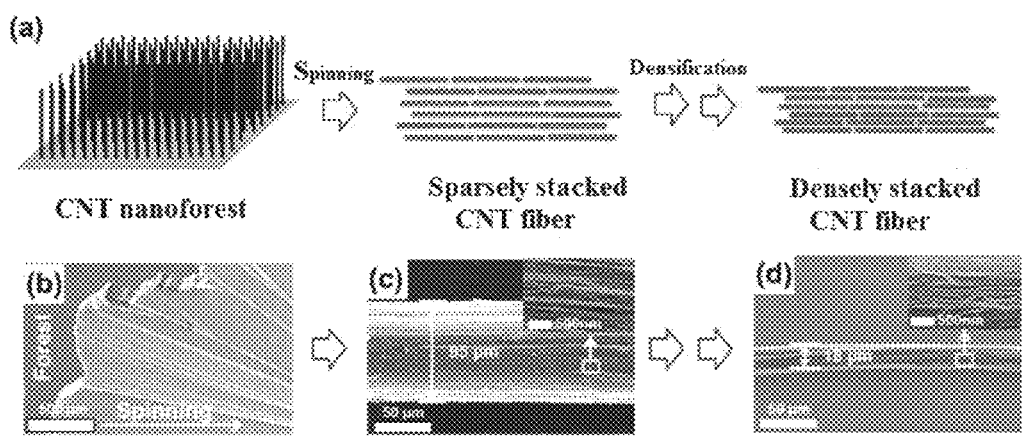

[Fig. 5]
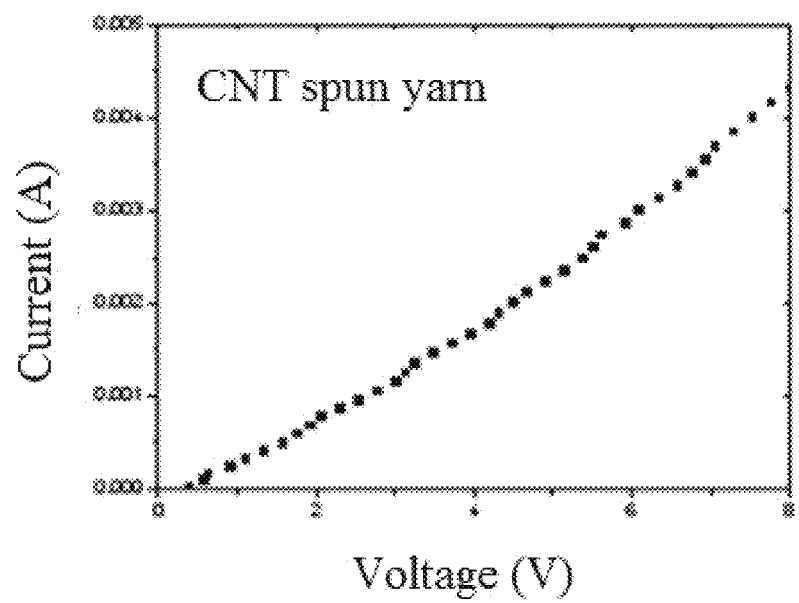

[Fig. 6]
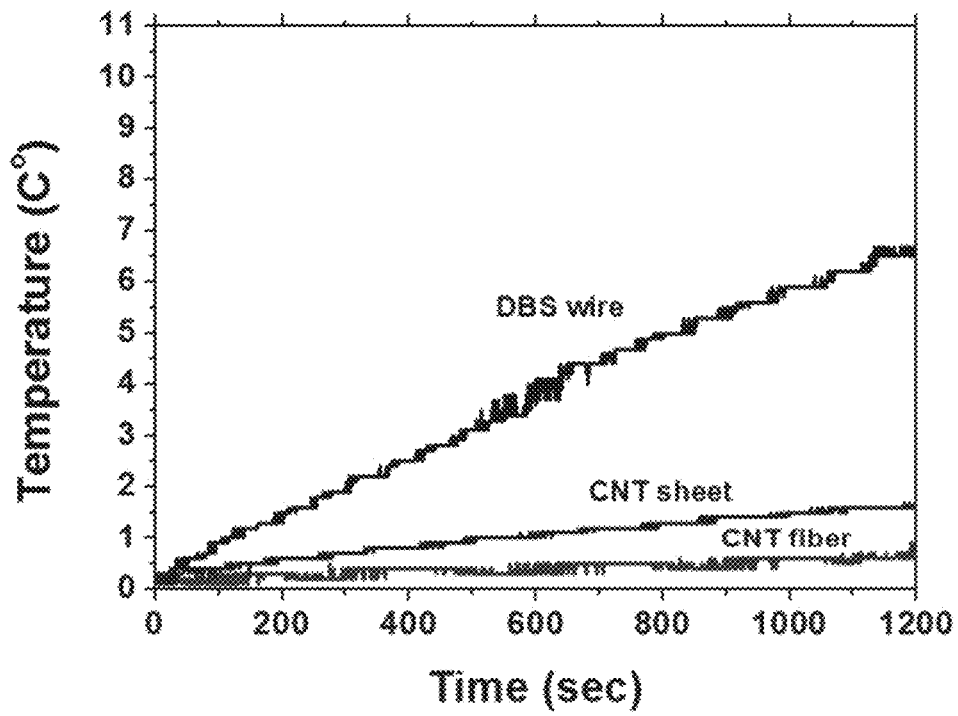
[Fig. 7]
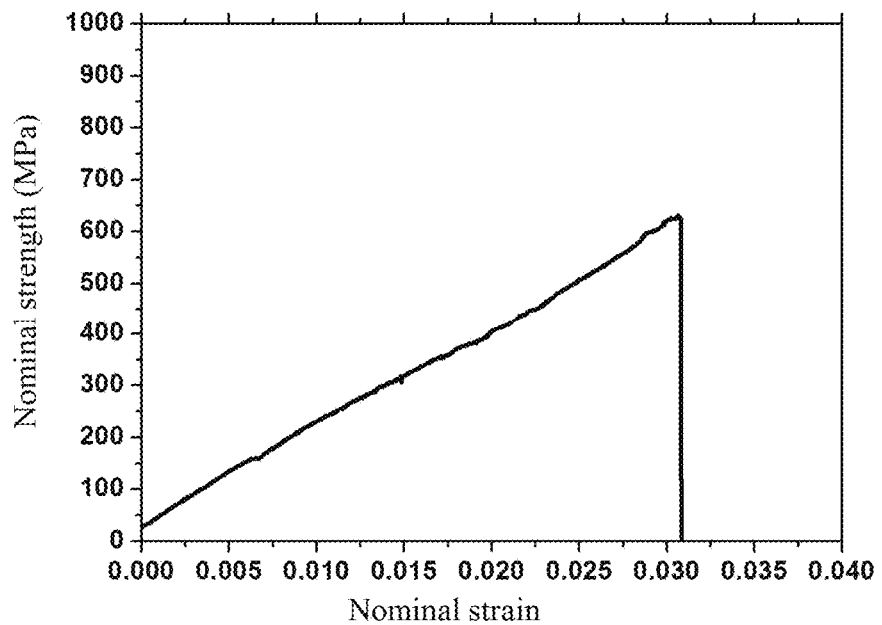

BIO-IMPLANTABLE ELECTRODE ASSEMBLY

CROSS-REFERENCE TO RELATED APPLICATIONS

This application is the U.S. National Phase under 35 U.S.C. § 371 of International Application No. PCT/KR2014/004972 filed on Jun. 3, 2014, which in turn claims the benefit of Korean Application No. 10-2013-0064275, filed on Jun. 4, 2013, the disclosures of which are incorporated by reference into the present application.

TECHNICAL FIELD

The present invention relates to a bio-implantable electrode assembly. More particularly, the present invention relates to a bio-implantable electrode assembly that can be safely operated in a magnetic field and has excellent mechanical properties, and a neurostimulation device including the same.

BACKGROUND ART

Nowadays, bio-implantable medical devices are used to treat various diseases. Some of the bio-implantable medical devices are based on neurostimulation as a therapeutic principle and can be used for the treatment and management of diseases, such as pain, constipation, sleep disturbances, Parkinson's disease, epilepsy, hand tremor, and myodystonia. Representative examples of such neurostimulation devices include spinal cord stimulation (SCS) systems and deep brain stimulation (DBS) systems.

FIG. 1 is a schematic diagram of a deep brain stimulation system and shows a state in which a neurostimulation electrode applies a neural stimulus to the thalamus. A neurostimulation-based bio-implantable medical device, such as an SCS or DBS device, essentially includes a neurostimulator adapted to generate pulse signals for electrical neurostimulation and at least one electrode inserted into a nerve site in need of treatment and through which the neurostimulation signals are applied to the nerve site (see FIG. 1). The neurostimulation electrode of the DBS device exemplified in FIG. 1 penetrates the cranium but it is to be understood that the neurostimulation electrode may also be inserted or implanted into any specific nerve site of the spinal cord, the peripheral nervous system or the brain. For example, a bio-implantable electrode of an SCS device may be inserted so as to penetrate the greater pectoral muscle, abdomen or buttock of a patient. In the neurostimulation-based bio-implantable device, the at least one electrode is usually connected to a long lead, as shown in FIG. 1. The lead is responsible for the electrical connection between the electrode and the neurostimulator. The electrode of the device is often inserted into the subcutaneous tissue layer of the patient. In many practical cases, however, the nerve coming into contact with the electrode is positioned deeper in the body. Thus, a connector is provided to connect the neurostimulator to the lead. In many cases, the neurostimulator and the connector are positioned outside the body.

Such an implantable or insertable electrode is used for neurostimulation but should not be reduced in size below a predetermined limit in order to effectively conduct electricity. Accordingly, the electrode cannot be inserted into the body without a relatively extensive surgical incision. For example, DBS treatment requires an extensive incision of the scalp and cranium of a patient. This incision should be made under general anesthesia and causes great inconvenience for the patient.

Highly elastic metals and alloys, such as gold, stainless steel, tungsten, and platinum-iridium alloys, are currently used to produce electrodes for neurostimulation but they are not satisfactory in bioaffinity. When such a highly elastic metal or alloy is used as an electrode material, it tends to react with body fluids. This reaction causes the corrosion of the electrode material in the body, which leads to the limited service life of the electrode. Also, the patient may suffer from pain and inflammation due to the corroded electrode.

Due to its relatively large size, the electrode delivers stimuli to a wide range of sites as well as a target site in the cerebral cortex and should apply strong stimuli to achieve a desired level of stimulation. Further, the production of the electrode requires the construction of a mold and process variations depending on the size and shape of the electrode, which are rather troublesome problems.

Moreover, a combination of neurostimulation therapy and diagnosis by magnetic resonance imaging (MRI) is being increasingly used to observe the therapeutic effect of neurostimulation. MRI is a noninvasive diagnostic tool that provides high resolution 3-dimensional images. However, patients are exposed to a rather strong electromagnetic field during MRI. The intensity of the electromagnetic field increases with increasing resolution of the MRI system. The MRI system emits a static magnetic field, a gradient magnetic field, and a radio-frequency magnetic field, which is generated from the transmitter of the scanner. That is, the MRI system emits a total of three magnetic field components. The static magnetic field has an intensity of about 0.2 to about 3.0 Tesla (T). 3.0 T corresponds to about 60,000 times greater than the earth's magnetic field. The intensity of the gradient magnetic field varies with time. 0 to 5 kHz can produce a gradient magnetic field of 40 mT/m. The radio frequency magnetic field is large in scale and can output a maximum energy of 20,000 W (corresponding to 20 times or more that of a toaster) with 64 MHz at a static magnetic field of 1.5 T. The magnetic fields of the MRI system adversely affect a neurostimulation device. For example, the static magnetic field applies a force to the neurostimulation device placed in the scanner of the MRI system. As a result, the neurostimulation device may be stressed. The radio-frequency magnetic field heats the metal parts of the neurostimulation device. Further, the time-dependent gradient magnetic field gives rise to an induced current, causing damage to the neurostimulation device and imaging disturbances. The most serious negative effect of the magnetic fields is that the lead of the neurostimulation device may be overheated by the radio-frequency magnetic field. Some research results reveal that the temperature of the lead is raised to 25° C. or above. The negative effects of the magnetic field of MRI systems on neurostimulation devices can be found, for example, in Rezai et al., *Journal of Magnetic Resonance Imaging*, Vol. 15(2002), pp. 241-250.

There is a need in the art for electrode materials that can be safely operated in the magnetic fields of an MRI system, have excellent mechanical properties, are sufficiently thin, and can replace metal materials, but the need is still not met.

DETAILED DESCRIPTION OF THE INVENTION

Problems to be Solved by the Invention

One object of the present invention is to provide a bio-implantable electrode material that is thinner than metal electrode materials while possessing excellent mechanical properties, thus being suitable for use in a bio-implantable electrode. A further object of the present invention is to provide a bio-implantable electrode material with high electrical conductivity that releases a reduced amount of heat in a high magnetic field environment.

Means for Solving the Problems

Aspects of the present invention provide a carbon fiber material for a neurostimulation electrode and a bio-implantable electrode including the carbon fiber material. The carbon fiber material is composed of a carbon fiber with a thickness of 1 to 1000 μm, a linear density of 0.01 to 5.00 g/cm, and an aspect ratio of 100 to 1,000,000. In one embodiment of the present invention, the carbon fiber is a carbon nanotube spun yarn. In one specific embodiment of the present invention, the carbon nanotube spun yarn is obtained by dry spinning carbon nanotubes as raw materials into a low-density nanotube spun yarn, followed by liquid-based densification. In one specific embodiment of the present invention, the carbon nanotube spun yarn has a tensile strength in the range of 10 to 100,000 MPa.

In a further aspect of the present invention, a bio-implantable electrode assembly is provided which includes an electrode inserted into the body to deliver electrical signals to a desired nerve site, an insulator coating surrounding on the surface of the electrode which leaves at least some portion of the electrode exposed, and a neurostimulation portion defined by the exposed portion of the electrode in which the electrical signals are applied to the nerve site upon contact, wherein the electrode is composed of a carbon fiber.

In another aspect of the present invention, there is provided a neurostimulation device including the above-mentioned bio-implantable electrode assembly, a neurostimulator adapted to generate pulse signals, and a connector through which the electrode assembly is wired or wirelessly connected to the neurostimulator.

Effects of the Invention

The carbon material of the present invention is thinner than metal electrode materials while possessing sufficient mechanical strength, thus being suitable for use in a bio-implantable electrode. Due to these advantages, the electrode assembly and the bio-implantable neurostimulation device of the present invention can be exactly directed to a nerve site to be stimulated. In addition, the carbon material of the present invention has high electrical conductivity and can minimize the generation of an induced current in a high magnetic field environment, such as a magnetic resonance imaging system, and the generation of heat by magnetic loss.

BRIEF DESCRIPTION OF THE DRAWINGS

FIG. 1 is a schematic diagram showing a state in which a general deep brain stimulation system is in use.

FIG. 2 is a schematic view of an electrode assembly according to one embodiment of the present invention.

FIG. 3 is a schematic view of an electrode assembly according to a further embodiment of the present invention.

FIG. 4 shows a method for preparing a carbon nanotube spun yarn according to one embodiment of the present invention and electron microscopy images revealing the experimental results obtained in the individual steps of the process; (a) a schematic diagram showing a method for preparing a nanotube spun yarn from a nanoforest of carbon nanotubes; (b) a scanning electron microscopy image showing a direction in which carbon nanotubes are spun from the nanoforest; (c) a scanning electron microscopy image showing a low-density carbon nanotube spun yarn; (d) an electron microscopy image showing a spun yarn prepared by densification of the low-density spun yarn.

FIG. 5 is a graph showing the electrical conductivity of a carbon fiber composed of a carbon nanotube spun yarn according to one embodiment of the present invention.

FIG. 6 is a graph comparing the heat release profiles of a carbon fiber according to one embodiment of the present invention and a commercial electrode for deep brain stimulation in a magnetic resonance imaging system.

FIG. 7 is a strain-strength curve of a carbon fiber for an electrode according to one embodiment of the present invention, which was measured to evaluate the tensile strength and modulus of elasticity of the carbon fiber.

MODE FOR CARRYING OUT THE INVENTION

The present invention will now be described in detail. Prior to the detailed description of the invention, it should be understood that the terms and words used in the specification and claims are not to be construed as having common and dictionary meanings, but are construed as having meanings and concepts corresponding to the spirit of the invention in view of the principle that the inventor can define properly the concept of the terms and words in order to describe his/her invention with the best method.

As used herein, the term "carbon nanotube" refers to a macromolecule in the shape of a long thin tube whose diameter is on the order of 1 to 200 nm and whose length is on the order of micrometers to millimeters. If necessary, the term "carbon nanotube" is used herein to mean the presence of a small amount of an additive, such as a conductivity improver. If necessary, the term "carbon nanotube" as used herein is intended to include a carbon nanotube whose surface is modified with a surface modifier after synthesis. The term "carbon nanotube" as used herein may refer to a single-walled nanotube (SWNT) or a multi-walled nanotube (MWNT) in the context of the present invention. The term "carbon nanotube" may refer to one independent strand of carbon nanotubes that extends without being cut or a portion (a filament or strand) of a spun yarn constructed by interlacing carbon fibers.

Carbon nanotubes have a very high aspect ratio (length/diameter). For example, the aspect ratio may be in the range of 100 to 1,000, typically 80 to 300. Carbon nanotubes are less dense than diamond and graphite but have a mechanical strength tens of times that high-strength alloys. The electrical conductivity of carbon nanotubes is higher than that of copper. Carbon nanotubes possess a thermal conductivity of about 2 times higher than that of diamond. Carbon nanotubes are stable at a high temperature (about 750° C.). In addition to these ideal characteristics, carbon nanotubes are less heated by an electromagnetic field than metal materials, which is thought to be because electrons of carbon nanotubes are confined in the $sp^2$ hybrid orbital, unlike free electrons of metals.

When mass-produced carbon nanotubes are simply used as bulk materials, superior conductivity of the individual carbon nanotubes at a microscopic level is difficult to achieve. This is because a contact resistance is created between adjacent strands of the nanotubes in the bulk aggregate, leading to a reduction in the electrical conductivity of the nanotubes.

As a result of extensive research to find a technical solution to the problem associated with the contact resistance deteriorating the performance of a bulk nanotube aggregate, the inventors have succeeded in developing a carbon fiber-based electrode material with excellent characteristics of nanotubes by densification of a nanotube aggregate and finally arrived at the present invention.

One aspect of the present invention provides a carbon fiber as an electrode material for a neurostimulation device. The carbon fiber has a thickness of 1 to 1000 μm, a linear density of 0.01 to 5.00 g/cm, and an aspect ratio of 100 to 1,000,000. The carbon fiber may be used alone to produce an electrode for a neurostimulation device.

Since the carbon fiber of the present invention has a small thickness and a linear density within the respective ranges defined above, it has superior mechanical strength, elasticity, and electrical conductivity. The thickness of platinum-iridium electrodes, which are recognized as the most outstanding commercial electrodes for neurostimulation, are on the order of 1.27 mm. In contrast, the electrode material of the present invention is easily operable even at a thickness of 20 μm so that nerve sites can be significantly protected from unnecessary stimulation. In one specific embodiment of the present invention, the electrode material has a tensile strength of 10 to 100,000 MPa. Accordingly, the electrode material of the present invention can be used to produce an electrode that has a much higher tensile strength than platinum-iridium electrodes whose tensile strength lies within the range of 1000 to 1200 MPa. In addition, the use of the electrode material according to the present invention enables the production of an electrode that exhibits a wide range of physical properties, such as strength.

In one embodiment of the present invention, the carbon fiber as an electrode material for neurostimulation is a carbon nanotube spun yarn. In one embodiment, the nanotube spun yarn may be twisted. In a further embodiment, the nanotube spun yarn is one obtained by spinning without twisting. In a more specific embodiment, the carbon nanotube spun yarn is one obtained by liquid-based densification.

The nanotube spun yarn having not undergone densification is also referred to as a "low-density nanotube spun yarn". The term "low-density nanotube spun yarn" is used to distinguish from the nanotube spun yarn having not undergone densification from the nanotube spun yarn having undergone densification. The low-density nanotube spun yarn has a linear density of approximately 0.01 to 5.00 g/cm. As the low-density nanotube spun yarn, there may be exemplified a nanotube spun yarn obtained by drawing carbon nanotubes from an aggregate of vertically oriented carbon nanotubes, for example, a nanoforest, and spinning the drawn carbon nanotubes. The low-density nanotube spun yarn may have high contact resistance, which makes it difficult to sufficiently ensure high mechanical strength and electrical conductivity of the individual nanotubes.

In one specific embodiment of the present invention, the liquid-based densification is performed by dipping the low-density spun yarn in a volatile solvent and vaporizing the solvent. As a result of the liquid-based densification, the texture of the spun yarn is densified. When the carbon nanotube fiber impregnated with the volatile solvent is dried, the nanotube strands become dense by surface tension and the spaces between the strands are reduced. In the densified nanotube spun yarn, load transfer between the constituent carbon nanotube strands is facilitated so that the inherent excellent mechanical properties of the carbon nanotubes can be easily exhibited. A smaller number of electron hopping paths are present in the densified spun yarn than in the low-density carbon nanotube spun yarn, contributing to an improvement in the conductivity of the densified spun yarn. To sum up, the carbon nanotube spun yarn having undergone densification can exhibit excellent electrical, mechanical, and thermal properties close to those of micrometer- to nanometer-scale individual carbon nanotube filaments.

A further aspect of the present invention provides an electrode assembly including an electrode composed of the carbon fiber and an insulator coating coated on the electrode.

FIG. 2 is a schematic view of an electrode assembly according to one embodiment of the present invention. Referring to FIG. 2, the electrode assembly 200 includes an electrode 210 composed of the carbon fiber, preferably a carbon nanotube spun yarn, and an insulator coating 220 coated to surround the electrode 210. The insulator coating 220 surrounds the electrode as a whole such that at least a portion of the electrode is exposed to the outside. The insulator coating 220 serves to prevent the electrode from coming into electrical contact with the body. A neurostimulation portion 215 is defined by the exposed portion of the electrode. Electrical signals generated from a neurotransmitter can be delivered to a desired nerve site through the neurostimulation portion 215 upon contact with the nerve site. Korean Patent Publication No. 10-2010-0065678 describes a brain stimulation electrode using an electrode tip that is composed of nanostructures, unlike conventional rod-like metal electrodes. Specifically, the brain stimulation electrode includes a supporting part in the form of a metal wire and an electrode tip supported on the support. The electrode tip may be made of metallic or semimetallic materials, including carbon nanotubes. The electrode assembly 200 of the present invention is structurally different from the electrode structure described in the Korean patent publication. The electrode assembly 200 does not include a support and an electrode tip composed of nanostructures, which are distinctly separated from each other, and instead is composed of a carbon fiber as a whole. The brain stimulation electrode of the electrode assembly according to the present invention does not use a metal wire, whereas the prior art electrode suffers from overheating of the metal wire by a magnetic field of an MRI system.

The entire length of the electrode assembly 200 may vary according to the intended use and may be, for example, from 5 cm to 10000 cm. Preferably, the electrode assembly 200 has an entire length in the range of 50 cm to 1000 cm. Within this range, the electrode assembly 200 can efficiently minimize the generation of heat, enabling the delivery of stimuli from a battery to a target site in the deep brain. On the other hand, the neurostimulation portion 215 of the electrode 210 is from 0.01 cm to 5 cm, preferably from 0.1 to 1 cm in length. If the neurostimulation portion 215 is shorter than the lower limit defined above, it may not come into contact with a target site, resulting in weak stimulation of the target site. Meanwhile, if the neurostimulation portion 215 is longer than the upper limit defined above, stimuli may not be correctly delivered to a target site. A large portion of the body of the electrode 210 is covered with the insulator coating 220 and one end of the insulator coating 220 may remain uncovered and exposed, as illustrated in FIG. 2. In an alternative embodiment, neurostimulation portions 215 may be formed at positions other than both ends of the electrode 210. That is, a plurality of exposed portions of the electrode 210 may be arranged. For example, the insulator coating 220 may cover the entire surface of the electrode 210, including both ends of the electrode 210, and two to four exposed portions 215 of the electrode 210 may be arranged at uniform intervals. FIG. 3 is a schematic view of an electrode assembly according to a further embodiment of the present invention. Referring to FIG. 3, the electrode assembly 200 may be constructed such that four neurostimulation portions 215 are exposed.

In the electrode assembly 200 of the present invention, the electrode 210 serves to deliver electrical signals for neurostimulation to the neurostimulation portion 215 and to transmit and deliver electrical nerve signals detected by the neurostimulation portion 215 to an analyzer. The electrical signals for neurostimulation are generated from the outside. The electrode assembly 200 of the present invention may include an adaptor (not illustrated) through which the electrode 210 can be connected to an external neurostimulator or connector.

In the electrode assembly 200 of the present invention, the insulator coating 220 surrounds the entire surface of the electrode 210 and electrically insulates the electrode 210 from the body. The insulator coating 220 may be composed of an organic or inorganic material, typically a polymer resin. In one embodiment, the insulator coating 220 may be composed of a biocompatible polymer resin. Specific examples of suitable materials for the insulator coating 220 include phenolic resins, urea resins, melamine resins, unsaturated polyester resins, diaryl phthalates, epoxy resins, alkyd resins, polyimide, polyurethane, polyethylene, polypropylene, poly-4-methylpentene, polymethyl methacrylate, acrylonitrile resins, polyvinyl chloride, polyvinyl acetate, polyvinyl alcohol, polyvinyl butyral, polyvinylidene chloride, polystyrene, ABS resins, polyamide, polyacetal, polycarbonate, polyethylene terephthalate, polybutylene terephthalate, ionomer resins, polysulfone, polyethersulfone, polyphenylene ether, polyphenylene sulfide, polyetherimide, polyetheretherketone, aromatic polyester, thermoplastic urethane elastomers, fluorinated rubbers, ethylene tetrafluoride resins, ethylene trifluoride resins, polyvinylidene fluoride, polyvinyl fluoride, nitrocellulose, cellulose acetate, ethyl cellulose, propylene cellulose, and glass-reinforced fibers. The thickness of the insulator coating 220 may be in the range of 0.1 mm to 30 mm. If the insulator coating 220 is thinner than the lower limit defined above, the insulation effect of the insulator coating 220 is negligible. Meanwhile, if the insulator coating 220 is thicker than the upper limit defined above, the large volume of the insulator coating 220 may cause brain damage.

In one specific embodiment, the electrode of the electrode assembly is used for deep brain stimulation. In a more specific embodiment, the whole body of the electrode including the neurostimulation portion may be realized using a carbon nanotube spun yarn. For example, the carbon nanotube spun yarn may be prepared by spinning carbon nanotubes, as described in Example 1 that follows. The carbon nanotube spun yarn may be used without further processing as a material for the electrode. The electrode may be produced using carbon nanotubes or a graphene material having $sp^2$ bonds. In this case, the electrode may be produced in a bulk form by various processes, including solution-based processes (e.g., vacuum filtration and spray coating) and pressing, based on high intermolecular $\pi$-$\pi$ bonding strength of the electrode material. The same method for the production of the electrode may be applied to the production of a lead. The lead can be strongly connected to the carbon nanotubes through a polymer resin and a surface tension-based spinning process. The carbon nanotubes can be complexed with the polymer resin and per se can be used as materials for deep brain stimulation.

Another aspect of the present invention provides a bioimplantable neurostimulation device including the electrode assembly, a neurostimulator adapted to generate pulse signals, and a connector through which the electrode assembly is wired or wirelessly connected to the neurostimulator.

The neurostimulator is a device that generates electrical pulse signals for neurostimulation. The neurostimulator delivers pulse signals to the electrode through the connector. The neurostimulator of the neurostimulation device is not particularly limited and may be any of those commonly used in the art. In one embodiment, the neurostimulator includes a signal analyzer that analyzes nerve signals detected by the electrode. In one specific embodiment of the present invention, the neurostimulator of the neurostimulation device is based on a feedback control mechanism with the signal analyzer to appropriately feedback control neurostimulation pulse signals depending on the results of analysis of the detected nerve signals.

The connector is not limited to any specific construction and may be any of those commonly adopted in the art. In one embodiment of the present invention, the connector of the neurostimulation device may take the form of a wired lead, as shown in FIG. 1. Alternatively, the connector may wirelessly connect the electrode assembly to the neurostimulator. In this case, the connector may include a power supply unit that wirelessly transmits pulse signals from the neurostimulator. For example, the pulse signals may have frequencies of 1 kHz to 9999 GHz.

A further aspect of the present invention discloses a method for preparing the carbon fiber as an electrode material.

In one embodiment of the present invention, the carbon fiber is composed of a spun yarn obtained by dry spinning carbon nanotubes. In one specific embodiment, the carbon nanotube spun yarn may be obtained by dry spinning in which carbon nanotube strands are drawn from an aggregate of the carbon nanotube strands vertically aligned on a substrate. An aggregate of nanotubes vertically aligned on a substrate is commonly called a "nanotube forest" or "nanoforest". The vertically aligned nanotubes are merely illustrative and an aggregate of nanotubes aligned in a direction non-perpendicular to a substrate may also be used in the dry spinning based on the same principle. An aggregate of randomly oriented nanotubes can also be considered for the dry spinning.

According to the dry spinning, the nanotube strands are drawn from the nanoforest in a direction parallel to the plane of the substrate (in a direction orthogonal to the vertical alignment direction). At this time, the adjacent carbon nanotube filaments are also continuously extracted by the van der Waals attractive force between the carbon nanotubes to obtain a spun yarn. It is convenient to draw the carbon nanotubes in the direction orthogonal to the alignment direction of the nanotubes on the substrate. Alternatively, the carbon nanotubes may be drawn from the substrate along a direction inclined at an angle with respect to the plane of the substrate. The carbon nanotubes may be twisted upon drawing by one skilled in the art taking into consideration the desired mechanical strength and electrical conductivity. That is, the nanotube bundles may be drawn at a predetermined angle with respect to the drawing axis. This twisting increases the interaction between the carbon nanotube strands, and as a result, load transfer between the carbon nanotube strands is facilitated, leading to improved physical properties. The twisting angle can be easily determined through repeated experiments by one skilled in the art. In a further specific embodiment, the nanotube spun yarn is one obtained by spinning without twisting.

The nanoforest used for the preparation of the nanotube spun yarn is obtained by a suitable method well known in the art, and thus a brief explanation will be given of the method. A method for preparing a uniform aggregate of dense nanotubes vertically arranged on a substrate can be found, for example, in U.S. Pat. No. 6,361,861. Representative techniques for forming carbon nanotubes on a substrate are (1) chemical vapor deposition, (2) carbon arc discharge, and (3) laser ablation. Chemical vapor deposition, particularly plasma enhanced chemical vapor deposition (PECVD), is widely used due to its convenience of use. Chemical vapor deposition, for example, PECVD, is convenient to use for preparing carbon nanotubes as electrode materials because the type, length, diameter, and linearity of carbon nanotubes can be controlled independently. In one specific embodiment of the present invention, the characteristics of the electrode materials can be controlled in a relatively simple manner by controlling the reaction conditions for chemical deposition when compared to those of metal electrode materials.

The substrate underlying the nanoforest may be made of a material selected from aluminum, silicon, silicon oxide, and aluminum oxide. The thickness of the substrate is not particularly limited but is typically from 10 nm to 100 nm.

A reinforcing layer may be formed on the substrate. The reinforcing layer may be formed using a metal oxide or a metal other than the substrate material. Examples of suitable materials for the reinforcing layer include alumina, aluminum, and titanium oxide. The reinforcing layer may be formed by a sol-gel process or a general deposition process. Specific examples of deposition processes for the formation of the reinforcing layer include chemical vapor deposition, sputtering, evaporation, atomic layer deposition (ALD), and molecular-beam epitaxy (MBE). The thickness of the reinforcing layer is not particularly limited but is preferably from 10 nm to 100 nm.

A catalyst may be used for the formation of carbon nanotubes. The catalyst is provided on the substrate or the overlying reinforcing layer. The catalyst is not particularly limited and may be any of those commonly used in the art. Examples of such catalysts include iron, cobalt, nickel, iron-cobalt, iron-nickel, cobalt-nickel, iron-molybdenum, cobalt-molybdenum, and nickel-molybdenum. Oxides of these metals may also be used but reduction products thereof are preferably used due to their higher catalytic activity. The catalyst may be formed into a thin film. In this case, the thickness of the catalyst thin film may be, for example, from 0.5 to 2.0 nm. More preferably, the catalyst molecules are allowed to aggregate on portions of the surface of the catalyst layer to form points for the growth of carbon nanotubes. For example, portions of the surface of the catalyst layer are reduced to form aggregates of the catalyst molecules thereon.

In the present invention, all types of carbon nanotubes, including single-walled and multi-walled nanotubes, may be used. The height of the carbon nanotubes in the nanoforest is not particularly limited but is preferably from 10 to 500 μm. The linear density of the carbon nanotubes in the nanoforest is preferably from 0.5 g/cm to 2.0 g/cm.

The carbon nanotube spun yarn obtained from the nanoforest by dry spinning has a low density and thus needs to be densified. In one specific embodiment of the present invention, the low-density carbon nanotube spun yarn is densified using liquid-based densification. The liquid-based densification is performed by dipping the low-density spun yarn in a volatile solvent and vaporizing the solvent. For example, the volatile solvent may be selected from acetone, ethanol, methanol, isopropanol, toluene, chloroform, and chlorobenzene. As a result of the liquid-based densification, the low-density spun yarn can be converted to the carbon fiber of the present invention that is suitable as an electrode material. The carbon fiber has a thickness of 1 to 1000 μm, a linear density of 0.01 to 5.00 g/cm, and an aspect ratio of 100 to 1,000,000.

(a) of FIG. 4 is a schematic diagram showing the method for preparing a nanotube spun yarn, including: nanoforest formation→dry spinning→liquid-based densification. As shown in FIG. 4, an iron catalyst having a size of several nm is placed on a silicon/aluminum substrate, a nanoforest is formed on the substrate by PECVD, the nanoforest is dry spun (b) into obtain a low-density carbon nanotube fiber (spun yarn, (c)), followed by densification to obtain a desired carbon fiber (d). The bio-implantable electrode of the present invention, which is composed of the densified carbon nanotube spun yarn only, has a much higher electrical conductivity than general electrode metal materials. In one specific embodiment, the carbon fiber of the present invention has an electrical conductivity 1000 times higher than that of a metal electrode material.

The carbon fiber-based electrode material of the present invention can minimize the generation of an induced current in a high magnetic field environment, such as a magnetic resonance imaging system, and the generation of heat by magnetic loss, thus being suitable as a potential material for neurostimulation devices as well as deep brain stimulation devices.

EXAMPLES

The present invention will be explained in more detail with reference the following examples. However, these examples are provided for illustrative purposes only and the scope of the invention is not limited thereto.

A neurostimulation electrode according to one specific embodiment of the present invention was produced from nanotubes and its performance characteristics were evaluated.

Preparative Example 1

Preparation of Substrate for Nanoforest Formation

In this preparative example, a nanoforest as an arrangement of vertically aligned carbon nanotubes was formed. First, aluminum and iron were sequentially deposited to uniform thicknesses on a silicon substrate using a sputter under controlled voltage and current conditions. Specifically, aluminum was first deposited at a rate of 6.2 nm/min at 625 V and 0.05 A, and iron was subsequently deposited at a rate of 3.4 nm/min under the same voltage and current conditions until their final thicknesses reached 10 nm and 5 nm, respectively. The surface of the deposited iron catalyst was coarsened by heat treatment. Subsequently, plasma enhanced chemical vapor deposition (PECVD) using inductively coupled plasma (ICP) was performed and the surface of the iron catalyst particles was reduced by hydrogen.

Preparative Example 2

Synthesis of Vertically Aligned Carbon Nanotubes

In this preparative example, a nanoforest was formed on the substrate obtained by PECVD using ICP in Preparative Example 1. For the chemical vapor deposition process, ethylene was used as a carbon source, argon and hydrogen were used as auxiliary gases, and oxygen gas was used to stabilize the catalyst. Carbon nanotubes were synthesized at 730° C. for 7 min. At this time, the temperature was raised at a rate of 100° C./min. FIG. 4 shows a scanning electron microscopy (SEM) image of the nanoforest. The length of the nanotubes in the nanoforest was approximately 200 μm.

Example 1

Spinning of the Carbon Nanotubes

In this example, the vertically aligned carbon nanotubes obtained in Preparative Example 2 were dry spun to prepare a carbon fiber. First, the nanoforest obtained in Preparative Example 1 was connected to a spinner (custom-made, requested to ATEC System) using electron tweezers, and then the nanotubes on the substrate were drawn without twisting at a rate of 1 cm/min in a direction perpendicular to the lengthwise direction of the nanotubes ("dry spinning"). (b) of FIG. 4 is an image showing the direction of the dry spinning. The arrow ("spinning") in the image indicates the direction perpendicular to the lengthwise direction of the nanotubes. As a result of the dry spinning, a "low-density" carbon nanotube spun yarn was obtained. The sparsely stacked fiber had a thickness of about 95 μm ((c) of FIG. 4) and a linear density on the order of 0.2 g/cm. The aspect ratio of the low-density carbon nanotube spun yarn was about 2,000. Subsequently, the low-density carbon nanotube spun yarn was densified. The densification was performed using ethanol based on the inherent surface tension of carbon nanotubes. (d) of FIG. 4 is a scanning electron microscopy image of the densified carbon fiber. The densified carbon fiber had a thickness of about 18 μm, a linear density on the order of 0.5 g/m, and an aspect ratio of about 10,000.

Test Example 1

Measurement of Conductivity of the Carbon Fiber

In this test example, the electrical conductivity of the carbon fiber prepared in Example 1 was evaluated. First, the carbon fiber was cut into a specimen having a size of 3 cm (length)×18 μm (thickness). Both ends of the specimen were fixed to electrodes of a system for electrical conductivity measurement (CMT-SR2000, Changmin Tech Co., Ltd.) with a silver paste.

FIG. 5 is a graph showing the current-voltage characteristics of the carbon fiber. Referring to FIG. 5, the voltage of the carbon fiber increased steadily with increasing current, corresponding to the conductivity profile of a typical conductive fiber. Based on the conductivity profile, the carbon fiber was calculated to have an electrical conductivity of 515 S/cm, which corresponds to a maximum of at least 1000 times that of a commercial electrode for deep brain stimulation.

Test Example 2

Heat Release of the Carbon Fiber in Magnetic Resonance Imaging System

First, the carbon fiber prepared in Example 1 was processed in the same manner as in Test Example 1. The temperature rise of the carbon fiber in a magnetic resonance imaging (MRI) system was evaluated. To simulate an actual situation in which an electrode is inserted into the body, the carbon nanotube (CNT) fiber of Test Example 1, a carbon nanotube sheet (CNT conductive film, Toray advanced film Co.), and a DBS wire (DBS™ 3389, Medtronic Inc.) each was inserted into an agarose gel, which was then fixed onto an acrylic substrate. The specimen thus prepared was transferred to a 4.7 T MRI system for animal experiments. $T_1$ spin-echo scans were performed in the MRI system for about 20 min. At this time, the internal temperature of the agarose gel in the specimen was measured using a thermo-optic analyzer (4.7 T MRI for animals, Varian). The results are graphically presented in FIG. 6.

FIG. 6 shows the temperature profiles of the carbon nanotube fiber, the carbon nanotube sheet, and the commercial DBS metal wire. Referring to FIG. 6, the temperatures of the carbon nanotube fiber and the carbon nanotube sheet were increased by 0.7° C. and 1.1° C., respectively. The commercial DBS metal wire showed a temperature rise of 6° C. The carbon nanotube materials released small amounts of heat compared to the metal material. The carbon nanotube fiber released a smaller amount of heat than the carbon nanotube sheet. These results are thought to be due to the difference in the shape of the carbon nanotube structures.

Test Example 3

Measurement of Tensile Strength

The tensile strength of the carbon nanotube spun yarn prepared in Example 1 was evaluated at a rate of 0.1 mm/min using a 1 cm strain gauge (INSTRON 8032, Instron Corporation). FIG. 7 reveals that the carbon nanotube fiber had a high tensile strength of 620 MPa and a modulus of elasticity of 1.8 GPa.

Although the present invention has been described herein with reference to the foregoing specific description and some embodiments, it should be noted that the description and embodiments are merely illustrative and are provided to assist in a better understanding of the invention. The present invention is not limited to the illustrated embodiments. Those skilled in the art will appreciate that various changes and modifications can be made to these embodiments and such changes and modifications are encompassed within the scope and spirit of the present invention.

Therefore, the embodiments described above, the appended claims, and their equivalents or any equivalent changes fall within the scope and spirit of the invention.

The invention claimed is:

1. A bio-implantable electrode assembly comprising:
   an electrode inserted into a body to deliver electrical signals to a desired nerve site;
   an insulator coating on a surface of the electrode which leaves at least some portion of the electrode exposed; and
   a neurostimulation portion defined by the exposed portion of the electrode in which the electrical signals are applied to the nerve site upon contact, wherein the electrode is composed of a carbon fiber,
   wherein the carbon fiber has a thickness of 1 to 1000 μm, a linear density of 0.01 to 5.00 g/cm, and an aspect ratio of 100 to 1,000,000.

2. The bio-implantable electrode assembly according to claim 1, wherein the carbon fiber is a carbon nanotube spun yarn.

3. The bio-implantable electrode assembly according to claim 2, wherein the carbon nanotube spun yarn is one obtained by liquid-based densification.

4. The bio-implantable electrode assembly according to claim 2, wherein the carbon nanotubes are single-walled carbon nanotubes (SWNTs), multi-walled carbon nanotubes (MWNTs) or a mixture thereof.

5. The bio-implantable electrode assembly according to claim 2, wherein the carbon nanotube spun yarn has a tensile strength of 10 to 100,000 MPa.

6. A neurostimulation device comprising the bio-implantable electrode assembly according to claim 1, a neurostimulator adapted to generate pulse signals, and a connector through which the electrode assembly is wired or wirelessly connected to the neurostimulator.

7. The neurostimulation device according to claim 6, wherein the pulse signals have frequencies of 1 kHz to 9999 GHz.

8. The bio-implantable electrode assembly according to claim 1, wherein the insulator coating is composed of a biocompatible polymer resin.

9. The bio-implantable electrode assembly according to claim 1, wherein the thickness of the insulator coating is in a range of 0.1 mm-20 mm.

10. The bio-implantable electrode assembly according to claim 1, wherein the carbon fiber consists of a circumferential surface and two end surfaces and the insulator coating encloses the entire circumferential surface of the carbon fiber except for the neurostimulation portion.

11. The bio-implantable electrode assembly according to claim 1, wherein the neurostimulation portion is located at an end of the electrode.

12. The bio-implantable electrode assembly according to claim 1, wherein the electrical signals are delivered to the desired nerve site only through the carbon fiber electrode.

13. The bio-implantable electrode assembly according to claim 6, wherein the electrical signals are delivered to the desired nerve site only through the carbon fiber electrode.

* * * * *